(12) United States Patent
Warby

(10) Patent No.: US 8,616,197 B2
(45) Date of Patent: Dec. 31, 2013

(54) DISPENSING APPARATUS

(75) Inventor: Richard Warby, Cambridgeshire (GB)

(73) Assignee: Consort Medical PLC, Hemel Hempstead (GB)

( * ) Notice: Subject to any disclaimer, the term of this patent is extended or adjusted under 35 U.S.C. 154(b) by 480 days.

(21) Appl. No.: 12/858,979

(22) Filed: Aug. 18, 2010

(65) Prior Publication Data

US 2011/0048418 A1   Mar. 3, 2011

(30) Foreign Application Priority Data

Sep. 1, 2009   (GB) .................................. 0915197.8

(51) Int. Cl.
| | |
|---|---|
| A61M 11/00 | (2006.01) |
| A61M 15/00 | (2006.01) |
| A61M 16/00 | (2006.01) |
| A61M 16/10 | (2006.01) |
| A62B 7/06 | (2006.01) |
| A62B 7/00 | (2006.01) |
| A62B 18/00 | (2006.01) |
| B67D 7/22 | (2010.01) |
| G01D 11/00 | (2006.01) |

(52) U.S. Cl.
USPC ............ 128/200.23; 128/200.14; 128/200.24; 128/203.12; 222/38; 116/285

(58) Field of Classification Search
USPC .................... 128/200.14, 200.21–23, 203.12, 128/203.15, 203.16, 203.21, 203.23, 128/200.24; 604/68–72; 222/23, 36–38, 222/635; 116/306, 307, 309, 311–320, 285; 137/551, 553, 556, 556.3, 556.6, 557; 235/1 A, 1 B, 60 C
See application file for complete search history.

(56) References Cited

U.S. PATENT DOCUMENTS

| | | | |
|---|---|---|---|
| 5,482,030 A | 1/1996 | Klein | |
| 6,138,669 A * | 10/2000 | Rocci et al. | ............. 128/200.23 |
| 6,907,876 B1 | 6/2005 | Clark et al. | |
| 7,467,629 B2 * | 12/2008 | Rand | ........................ 128/200.14 |
| 7,914,499 B2 * | 3/2011 | Gonnelli et al. | ............. 604/186 |
| 2007/0277817 A1 | 12/2007 | Innocenzi | |
| 2007/0284383 A1 | 12/2007 | Wright et al. | |
| 2008/0029085 A1 * | 2/2008 | Lawrence et al. | ........ 128/200.14 |

FOREIGN PATENT DOCUMENTS

| | | |
|---|---|---|
| EP | 1 088 567 | 4/2001 |
| GB | 1 383 649 | 2/1974 |
| GB | 2 348 928 | 10/2000 |
| GB | 2 433 207 | 6/2007 |

(Continued)

OTHER PUBLICATIONS

Combined Search and Examination Report under Section 17 an 18(3) mailed on Jan. 4, 2010 for GB0915197.8.

*Primary Examiner* — Jackie Ho
*Assistant Examiner* — Mark K Han
(74) *Attorney, Agent, or Firm* — Smith, Gambrell & Russell, LLP

(57) ABSTRACT

A dose counter system, and a dispensing apparatus having such a dose counter system, for counting activations of a pressurised dispensing container including: a hydraulic system; and a counter; the hydraulic system having a hydraulic cylinder with a primary piston, a secondary piston and a working fluid, wherein the secondary piston is coupled to, or otherwise operates the counter and the primary piston is engaged by, fixed to, coupled to, or otherwise moved by, a pressurised dispensing container.

16 Claims, 2 Drawing Sheets

(56) References Cited

FOREIGN PATENT DOCUMENTS

| GB | 2 438 396 | 11/2007 |
| WO | 98/56444 | 12/1998 |
| WO | 03/051438 | 6/2003 |
| WO | 2009/029028 | 3/2009 |

* cited by examiner

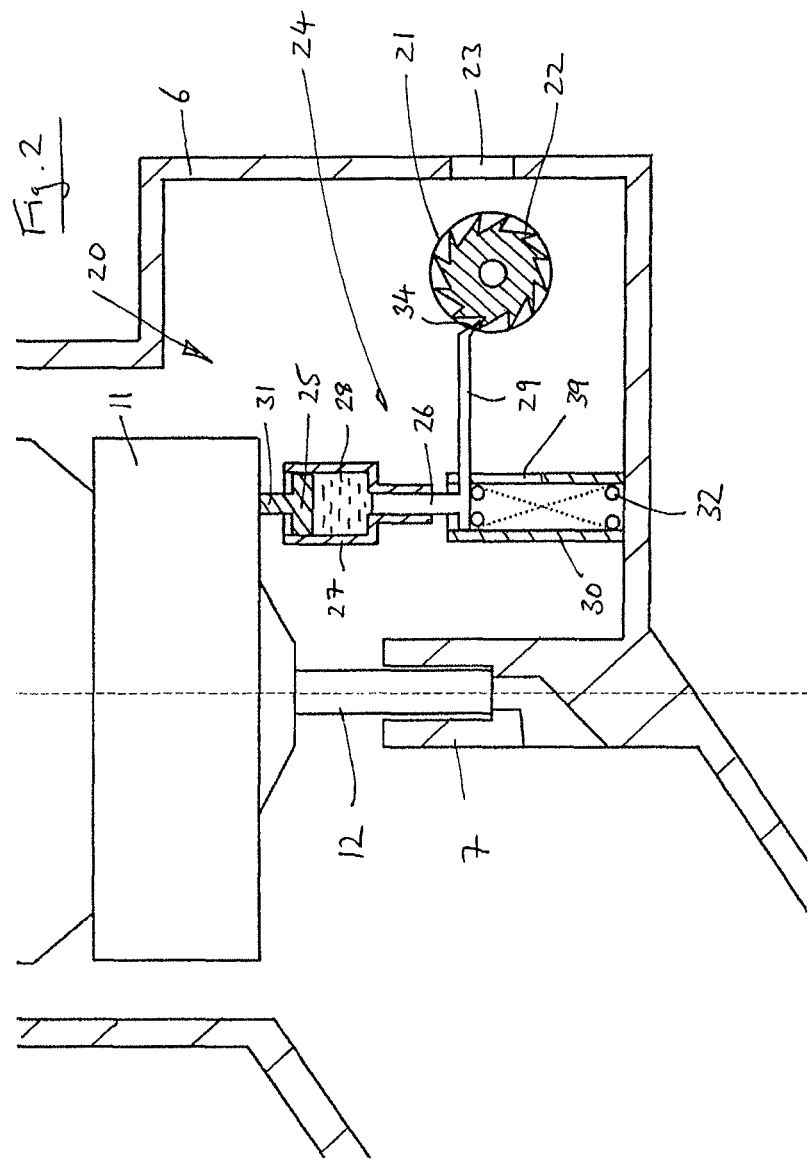

DISPENSING APPARATUS

FIELD OF THE INVENTION

The present invention relates to a dispensing apparatus having a hydraulic system for activating a dose counter based on movement of a received pressurised dispensing container. In particular, the invention relates to improvements in apparatus and dose counters for use in dispensing metered doses of pharmaceutical formulations or products from metered dose inhalers.

BACKGROUND

Dispensing apparatus such as metered dose inhalers are well known in the art for use in dispensing products such as pharmaceutical formulations for the treatment of respiratory conditions including asthma. A metered dose inhaler typically comprises an actuator housing in which is received a pressurised dispensing container which itself comprises a dispensing canister and a metering valve which are assembled together by means of a ferrule. The pressurised dispensing container contains a product to be dispensed and a propellant which is volatile at atmospheric conditions. An example of a metered dose inhaler of this type is described in the applicant's European patent application EP1088567. It is desirable to provide such a dispensing apparatus with a dose counter to provide an indication to a user of how many doses of product either remain in the pressurised dispensing container or have been dispensed from the pressurised dispensing container. In the past, a number of mechanical dose counters for such apparatus have been proposed. Examples are described in the applicant's patent applications GB2348928 and GB2438396. For mechanical dose counters for use with metered dose inhalers it is typical to use the linear movement of the pressurised dispensing container within the actuator housing for triggering or activating the mechanical dose counter mechanism. The metering valve of the pressurised dispensing container comprises a valve stem which protrudes and engages with a valve stem receiving block of the actuator housing. For a typical metering valve which is used in such applications the degree to which the valve stem travels in use relative to the remainder of the metering valve is relatively small and in the order of 3.5 mm. In addition, the travel of the valve stem before actuation of the valve is typically only in the order of 1.5 to 2.0 mm. This has been found to lead to problems in designing efficient and reliable mechanical dose counter mechanisms in that the relatively small physical travel of the valve stem, and hence the remainder of the pressurised dispensing container on actuation provides only limited physical movement of the pressurised dispensing container for triggering a mechanical dose counter mechanism.

SUMMARY OF THE INVENTION

It is therefore an object of the present invention to provide a mechanism which provides more reliable triggering of dose counters for dispensing apparatus and in particular mechanical dose counter mechanisms which are to be activated by movement of a device that has relatively limited travel.

Accordingly, the present invention provides a dispensing apparatus comprising:
 a housing suitable to receive in use a pressurised dispensing container capable of dispensing metered doses of a product; and
 a dose counter;
wherein the dispensing apparatus further comprises a hydraulic system for activating the dose counter based on movement of the received pressurised dispensing container.

Advantageously, the use of the hydraulic system allows the relatively limited movement of the pressurised dispensing container to be converted into a sufficient movement for triggering the dose counter.

Preferably, the hydraulic system comprises a hydraulic cylinder comprising a primary piston, a secondary piston and a working fluid.

In use, the primary piston may be engaged by, fixed to, coupled to, or otherwise moved by, the received pressurised dispensing container.

The secondary piston may comprise, or be coupled to, or otherwise move, a trigger, wherein the trigger is operative to activate the dose counter.

Preferably a working cross-sectional area of the secondary piston is less than a working cross-sectional area of the primary piston such that movement of the primary piston by a unit distance produces a movement of the secondary piston that is greater than unit distance.

The dose counter may be a mechanical dose counter.

The mechanical dose counter may comprise a counter wheel.

The hydraulic system may be located within the housing beneath the received pressurised dispensing apparatus.

Preferably the received pressurised dispensing container comprises a dispensing canister, a metering valve and a ferrule and the hydraulic system is engaged by, fixed to, or coupled to, the ferrule of the received pressurised dispensing container.

The present invention also provides a combination of a dispensing apparatus as claimed in any preceding claim and a pressurised dispensing container comprising a dispensing canister, a metering valve and a ferrule.

The present invention further provides a dose counter for counting activations of a pressurised dispensing container comprising:
 a hydraulic system; and
 a counter;
 the hydraulic system comprising a hydraulic cylinder with a primary piston, a secondary piston and a working fluid, wherein the secondary piston is coupled to, or otherwise operates the counter and the primary piston is engaged by, fixed to, coupled to, or otherwise moved by, a pressurised dispensing container.

Preferably a working cross-sectional area of the secondary piston is less than a working cross-sectional area of the primary piston such that movement of the primary piston by a unit distance produces a movement of the secondary piston that is greater than unit distance.

The dose counter may form an integral part of a dispensing apparatus.

The dose counter may further comprise a dose counter housing at least partially enclosing the hydraulic system and the counter to form a hydraulic dose counter unit.

The dose counter may be adapted to be removeably, semi-permanently or permanently attached to a pressurised dispensing container.

The dispensing apparatus may be, for example, a pulmonary, nasal, or sub-lingual delivery device. A preferred use of the dispensing apparatus is in a pharmaceutical metered dose aerosol inhaler device. The term pharmaceutical as used herein is intended to encompass any pharmaceutical, compound, composition, medicament, agent or product which can be delivered or administered to a human being or animal, for example pharmaceuticals, drugs, biological and medicinal products. Examples include antiallergics, analgesics, bronchodilators, antihistamines, therapeutic proteins and peptides, antitussives, anginal preparations, antibiotics, anti-inflammatory preparations, hormones, or sulfonamides, such as, for example, a vasoconstrictive amine, an enzyme, an alkaloid, or a steroid, including combinations of two or more thereof. In particular, examples include isoproterenol [alpha-(isopropylaminomethyl) protocatechuyl alcohol], phenylephrine, phenylpropanolamine, glucagon, adrenochrome, trypsin, epinephrine, ephedrine, narcotine, codeine, atropine, heparin, morphine, dihydromorphinone, ergotamine, scopolamine, methapyrilene, cyanocobalamin, terbutaline, rimiterol, salbutamol, flunisolide, colchicine, pirbuterol, beclomethasone, orciprenaline, fentanyl, and diamorphine, streptomycin, penicillin, procaine penicillin, tetracycline, chlorotetracycline and hydroxytetracycline, adrenocorticotropic hormone and adrenocortical hormones, such as cortisone, hydrocortisone, hydrocortisone acetate and prednisolone, insulin, cromolyn sodium, and mometasone, including combinations of two or more thereof.

The pharmaceutical may be used as either the free base or as one or more salts conventional in the art, such as, for example, acetate, benzenesulphonate, benzoate, bircarbonate, bitartrate, bromide, calcium edetate, camsylate, carbonate, chloride, citrate, dihydrochloride, edetate, edisylate, estolate, esylate, fumarate, fluceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate, (embonate), pantothenate, phosphate, diphosphate, polygalacturonate, salicylate, stearate, subacetate, succinate, sulphate, tannate, tartrate, and triethiodide, including combinations of two or more thereof. Cationic salts may also be used, for example the alkali metals, e.g. Na and K, and ammonium salts and salts of amines known in the art to be pharmaceutically acceptable, for example glycine, ethylene diamine, choline, diethanolamine, triethanolamine, octadecylamine, diethylamine, triethylamine, 1-amino-2-propanol-amino-2-(hydroxymethyl)propane-1,3-diol, and 1-(3,4-dihydroxyphenyl)-2 isopropylaminoethanol.

The pharmaceutical will typically be one which is suitable for inhalation and may be provided in any suitable form for this purpose, for example as a solution or powder suspension in a solvent or carrier liquid, for example ethanol, or isopropyl alcohol. Typical propellants are HFA134a, HFA227 and di-methyl ether.

The pharmaceutical may, for example, be one which is suitable for the treatment of asthma. Examples include salbutamol, beclomethasone, salmeterol, fluticasone, formoterol, terbutaline, sodium chromoglycate, budesonide and flunisolide, and physiologically acceptable salts (for example salbutamol sulphate, salmeterol xinafoate, fluticasone propionate, beclomethasone dipropionate, and terbutaline sulphate), solvates and esters, including combinations of two or more thereof. Individual isomers such as, for example, R-salbutamol, may also be used. As will be appreciated, the pharmaceutical may comprise of one or more active ingredients, an example of which is flutiform, and may optionally be provided together with a suitable carrier, for example a liquid carrier. One or more surfactants may be included if desired.

The seals and gaskets of the pressurised dispensing container may be formed from any suitable material having acceptable performance characteristics. Preferred examples include nitrile, EPDM and other thermoplastic elastomers, butyl and neoprene.

Other rigid components of the pressurised dispensing container, such as the valve body, valve member and valve stem may be formed, for example, from polyester, nylon, acetal or similar. Alternative materials for the rigid components of the pressurised dispensing container include stainless steel, ceramics and glass.

BRIEF DESCRIPTION OF THE DRAWINGS

An embodiment of the present invention will now be described, by way of example only, with reference to the accompanying drawings and which:

FIG. 2 is an enlarged schematic cross sectional representation of a portion of the apparatus of FIG. 1.

DETAILED DESCRIPTION OF THE INVENTION

Figure 1:
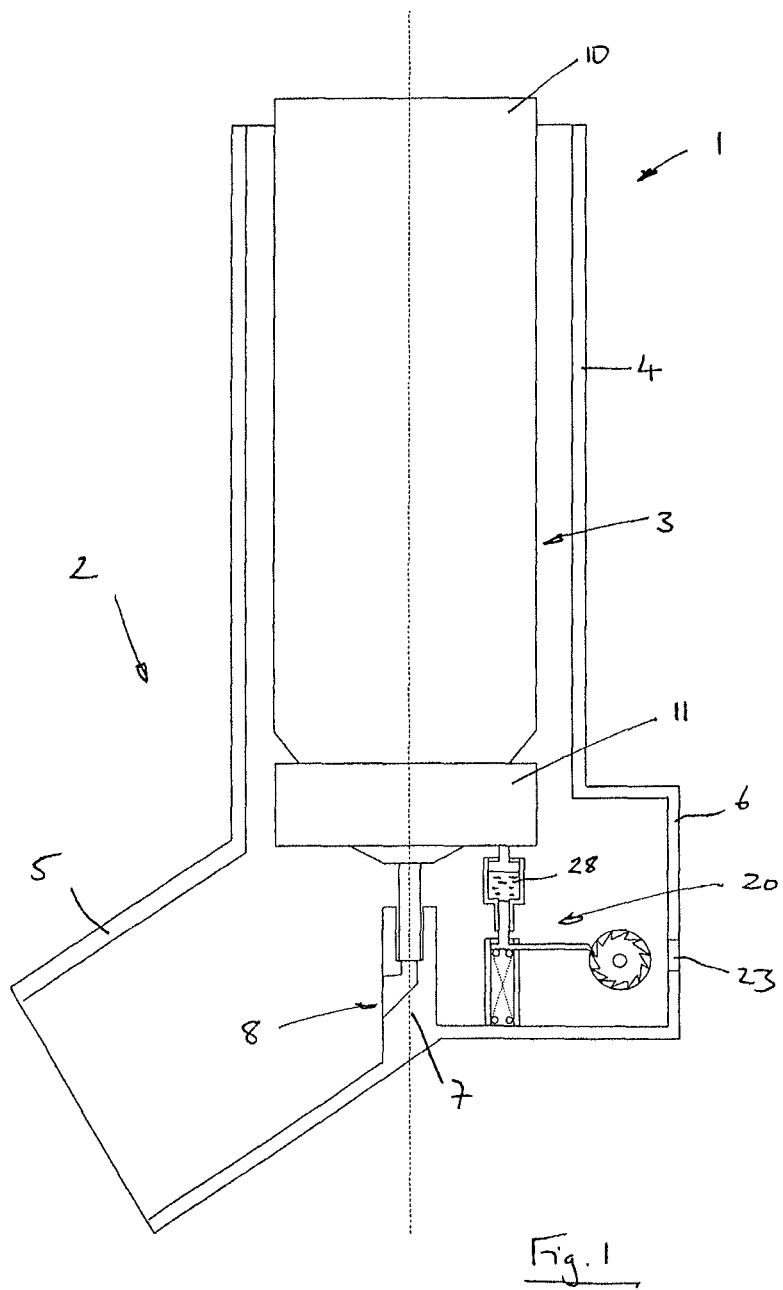
FIG. 1 is a schematic cross sectional representation of a dispensing apparatus according to the present invention together with a pressurised dispensing container.

As shown in FIG. 1, the dispensing apparatus of the present invention comprises a housing 2 in which is received in use a pressurised dispensing container 3 in the form of a dispensing canister 10 and a metering valve 12 secured to the canister 10 by means of a ferrule 11.

The housing 2 comprises a cylindrical section 4 which is open at its upper end and houses in use the pressurised dispensing container 3. At a lower end of the cylindrical section 4 there is provided a mouthpiece section 5 which terminates in an outlet though which a product is dispensed in use. At a base of the cylindrical section 4 is provided a valve stem receiving block 7 which engagingly receives an outlet end of the valve stem of the metering valve 12 as shown in FIG. 1. The valve stem receiving block 7 is provided with an outlet orifice 8 for directing product dispense from the metering valve towards the outlet of the mouthpiece 5.

In accordance with the present invention, the housing 2 is further provided with a counter housing section 6 in which is located a counter mechanism 20 which is shown in more detail in FIG. 2. Whilst in the illustrated embodiment the housing 2 is shown with an enlarged section 6 for receiving the counter mechanism 20, this is not essential and the counter mechanism 20 may be provided within the cylindrical section of a standard shaped housing.

The counter mechanism 20 is shown schematically in FIG. 2. The counter mechanism 20 comprises a means for counting the number of doses dispensed from or remaining within the pressurised dispensing container 3. In the illustrated example, a counter wheel 21 is provided rotatable mounted within the housing 2. The counter wheel 21 has marked on it periphery a series of numbers indicating the dose count which are viewable through a dose counter window 23 formed in the counter housing section 6. The counter wheel 21 is further provided with a series of teeth 22 which are disposed around the circumference of the counter wheel 21. The counter mechanism 20 further comprises a hydraulic activation mechanism 24. The hydraulic activation mechanism 24 comprises a hydraulic cylinder 27, a primary piston 25, a secondary piston 26 a trigger 29 and a support 30. The primary piston 25 is received in an upper end of the hydraulic cylinder 27 and the secondary piston 26 is received in a lower end of the hydraulic cylinder 27. Both pistons 25, 26 form fluid tight sliding seals with the hydraulic cylinder 27 in a known manner by use of components such as o-ring seals. The primary piston 25 is provided with an upper elongate extension 31. The secondary piston 26 is formed unitarily with the trigger 29 which is provided in the form of a laterally extending arm which terminates in a pawl 34 which engages the counter wheel 21 as will be described below. The hydraulic cylinder 27 is filled with a working fluid 28 such as oil.

The support 30 comprises an elongated tube having an open upper end which receives a lower end of the secondary piston 26 as shown in FIG. 2. The support 30 is further provided with a slot 39 in one side to accommodate the lateral extension of the trigger arm 29. A biasing spring 32 is provided within support 30 which extends from a base of the housing upwardly into contact with an under face of the secondary piston 26 in order to bias the secondary piston 26 upwards when viewed in the orientation shown in FIG. 2.

The figures show the dose counter 20 and hydraulic mechanism 24 schematically. In practice, supports for the dose counter wheel and hydraulic cylinder 27 would be necessary can could be provided as part of the moulded housing 2.

The working cross sectional area of the primary piston 25 is greater than the working cross sectional area of the secondary piston 26. By "working cross sectional area" is meant the area of the internal end face of a piston which is exposed to, and acted on by, the hydraulic fluid 28 of the hydraulic cylinder 27. For example, the working cross sectional area of the primary piston 25 may be 7.07 mm$^2$ (piston diameter of 3 mm) and the working cross sectional area of the secondary piston 26 may be 1.77 mm$^2$ (diameter of piston of 1.5 mm2).

The configuration of the hydraulic cylinder 27 in this way causes the secondary piston 26 to move a greater than unit distance on movement of the primary piston 25 through a unit distance. For example, for the working cross sectional areas given above, the 'distance multiplication factor' of the secondary piston 26 relative to the primary piston 25 is 7.07÷1.77=4. Thus, for each unit movement of the primary piston 25, the secondary piston 26 will move 4 units.

In use, activation of the pressurised dispensing container 3 by depressing the dispenser canister 10 manually will move the ferrule 11 downwards when viewed in the orientation shown in FIG. 2. The leading face of the ferrule 11 will engage the elongate extension 31 of the primary piston 25 and will depress the primary piston 25 within hydraulic cylinder 27. As noted above, this movement of the primary piston 25 within the hydraulic cylinder 27 will produce a larger movement of the secondary piston 26 which correspondingly moves the trigger arm 29 downwards relative to the counter wheel 21. Downward movement of the trigger arm 29 engages pawl 34 with one of the series of teeth 22 on the counter wheel 21 which causes the wheel 21 to rotate through an incremental amount to advance the dose count. Release of the pressurised dispensing container 3 allows the ferrule 11 to move upwardly under the internal spring biased of the metering valve 12. This disengages the ferrule 11 from the upper elongate extension 31 of the primary piston 25 which allows the hydraulic mechanism 24 to reset by virtue of the biasing effect of the spring 32. Resetting occurs because the biasing force of spring 32 acts upwardly on the secondary piston 26 to move the secondary piston 26 upwardly relative to the hydraulic cylinder barrel 27 and this upward force is transmitted to the primary piston 25 through the hydraulic working fluid 28. Upward movement of the trigger arm 29 causes the pawl 34 to move upwardly and ride over the neighbouring tooth 22 on the counter wheel 21. Counter-rotation of the counter wheel is prevented by standard means such as a ratchet (not shown).

Various modifications may be made to the inventive apparatus. The primary piston 25 may be fixed or coupled to the ferrule 11 rather than merely being engaged by the ferrule 11. For example, the upper elongate extension 31 may be welded to the ferrule 11. In such a case, resetting of the hydraulic mechanism 24 could be achieved without the requirement to provide a separate biasing means such as spring 32.

In a separate modification, the biasing means for resetting the hydraulic mechanism 24 may be provided by means of a spring located within the hydraulic cylinder 27 rather than in a separate support 30.

In the illustrated embodiment, the hydraulic mechanism 24 is illustrated as being provided in a section of the housing 2 underneath the received pressurised dispensing container 3. However, the hydraulic mechanism 24 may be located elsewhere in the dispensing apparatus 1. For example, the hydraulic mechanism 24 may be provided higher up within the cylindrical section 4 of the housing 2 alongside the canister 10 and engaged by a portion of the canister 10 (or a structure depending from the canister 10) rather than from the ferrule 11. Alternatively, the hydraulic mechanism 24 may be provided above the pressurised dispensing container 3. In a further alternative, the hydraulic mechanism 24 may be provided together with the counter mechanism as part of a separate housing which is coupled to a fixed or engaged with a housing containing the pressurised dispensing container 3.

The invention claimed is:

1. Dispensing apparatus comprising:
   a housing suitable to receive in use a pressurised dispensing container capable of dispensing metered doses of a product; and
   a dose counter;
   wherein the dispensing apparatus further comprises a hydraulic system for activating the dose counter, wherein the hydraulic system is configured to operate based on movement of the received pressurised dispensing container.

2. Dispensing apparatus as claimed in claim 1, wherein the hydraulic system comprises a hydraulic cylinder comprising a primary piston, a secondary piston and a working fluid.

3. Dispensing apparatus as claimed in claim 2 wherein, in use, the primary piston is engaged by, fixed to, coupled to, or otherwise moved by, the received pressurised dispensing container.

4. Dispensing apparatus as claimed in claim 2 wherein the secondary piston comprises, or is coupled to, or otherwise moves, a trigger, wherein the trigger is operative to activate the dose counter.

5. Dispensing apparatus as claimed in claim 2 wherein a working cross-sectional area of the secondary piston is less than a working cross-sectional area of the primary piston such that movement of the primary piston by a unit distance produces a movement of the secondary piston that is greater than the unit distance.

6. Dispensing apparatus as claimed in claim 1 wherein the dose counter is a mechanical dose counter.

7. Dispensing apparatus as claimed in claim 6 wherein the mechanical dose counter comprises a counter wheel.

8. Dispensing apparatus as claimed in claim 1 wherein the hydraulic system is located within the housing beneath the received pressurised dispensing container.

9. Dispensing apparatus as claimed in claim 1 wherein the received pressurised dispensing container comprises a dispensing canister, a metering valve and a ferrule and the hydraulic system is engaged by, fixed to, or coupled to, the ferrule of the received pressurised dispensing container.

10. A combination of a dispensing apparatus as claimed in claim 1, further comprising the pressurised dispensing container, the pressurised dispensing container comprising a dispensing canister, a metering valve and a ferrule.

11. Dispensing apparatus as claimed in claim 1, wherein the hydraulic system is a displacement multiplying hydraulic system.

12. A dose counter for counting activations of a pressurised dispensing container comprising:
   a hydraulic system; and
   a counter;
   wherein the hydraulic system comprises a hydraulic cylinder with a primary piston, a secondary piston and a working fluid, wherein the secondary piston is coupled to, or otherwise operates the counter and the primary piston is moved by the pressurised dispensing container.

13. A dose counter as claimed in claim 12 wherein a working cross-sectional area of the secondary piston is less than a working cross-sectional area of the primary piston such that movement of the primary piston by a unit distance produces a movement of the secondary piston that is greater than the unit distance.

14. A dose counter as claimed in claim 12 wherein the dose counter is an integral part of a dispensing apparatus.

15. A dose counter as claimed in claim 12 further comprising a dose counter housing at least partially enclosing the hydraulic system and the counter to form a hydraulic dose counter unit.

16. A dose counter as claimed in claim 15 wherein the dose counter is adapted for attachment to the pressurised dispensing container in a removable, semi-permanent or permanent manner.

\* \* \* \* \*